(12) United States Patent
Dalla Betta et al.

(10) Patent No.: US 7,641,653 B2
(45) Date of Patent: Jan. 5, 2010

(54) OPEN VESSEL SEALING FORCEPS DISPOSABLE HANDSWITCH

(75) Inventors: Casey D. Dalla Betta, Westminster, CO (US); J. Cody Bumgarner, Grand Junction, CO (US); Dylan Kingsley, Loveland, CO (US); John R. Twomey, Golden Valley, MN (US); Brady C. Walters, Littleton, CO (US); David M. Garrison, Longmont, CO (US); Dylan Hushka, Boulder, CO (US)

(73) Assignee: Covidien AG, Neuhausen Am Rheinfall (CH)

( * ) Notice: Subject to any disclaimer, the term of this patent is extended or adjusted under 35 U.S.C. 154(b) by 562 days.

(21) Appl. No.: 11/417,375

(22) Filed: May 4, 2006

(65) Prior Publication Data

US 2007/0260241 A1 Nov. 8, 2007

(51) Int. Cl.
*A61B 18/18* (2006.01)
*H01H 9/04* (2006.01)
(52) U.S. Cl. .................... 606/51; 200/293.1; 606/52
(58) Field of Classification Search ............. 606/32–35, 606/41, 42, 48–52; 200/293–295
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |

(Continued)

FOREIGN PATENT DOCUMENTS

CA 2104423 2/1994

(Continued)

OTHER PUBLICATIONS

Int'l Search Report EP 06 020574.7 dated Sep. 21, 2007.

(Continued)

*Primary Examiner*—Michael Peffley

(57) ABSTRACT

A removable handswitch and electrode assembly for use with a forceps having opposing end effectors and a handle for effecting relative movement of the end effectors with respect to one another includes a housing having at least one portion which removably engages at least a portion of a mechanical forceps and a handswitch assembly disposed on the housing. A pair of electrodes is included which removably engage a distal end of the mechanical forceps such that the electrodes reside in opposing relation to one another. At least one electrode is adapted to connect to an electrosurgical generator through the handswitch assembly. At least one stop member is operatively associated with the electrodes and controls the distance between the opposing electrodes to affect a tissue seal.

20 Claims, 12 Drawing Sheets

U.S. PATENT DOCUMENTS

| | | |
|---|---|---|
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A * | 2/1983 | Lottick ............... 606/42 |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |

| | | | | | |
|---|---|---|---|---|---|
| 5,558,672 A | 9/1996 | Edwards et al. | 5,827,271 A | 10/1998 | Buysse et al. |
| 5,562,699 A | 10/1996 | Heimberger et al. | 5,827,279 A | 10/1998 | Hughett et al. |
| 5,569,241 A | 10/1996 | Edwardds | 5,827,281 A | 10/1998 | Levin |
| 5,569,243 A | 10/1996 | Kortenbach et al. | 5,827,323 A | 10/1998 | Klieman et al. |
| 5,571,100 A | 11/1996 | Goble et al. | 5,827,548 A | 10/1998 | Lavallee et al. |
| 5,573,424 A | 11/1996 | Poppe | 5,833,690 A | 11/1998 | Yates et al. |
| 5,573,534 A | 11/1996 | Stone | 5,843,080 A | 12/1998 | Fleenor et al. |
| 5,573,535 A | 11/1996 | Viklund | 5,849,022 A | 12/1998 | Sakashita et al. |
| 5,575,805 A | 11/1996 | Li | 5,853,412 A | 12/1998 | Mayenberger |
| 5,578,052 A | 11/1996 | Koros et al. | 5,860,976 A | 1/1999 | Billings et al. |
| 5,582,611 A | 12/1996 | Tsukagoshi et al. | 5,876,401 A | 3/1999 | Schulze et al. |
| 5,585,896 A | 12/1996 | Yamazaki et al. | 5,882,567 A | 3/1999 | Cavallaro et al. |
| 5,590,570 A | 1/1997 | LeMaire, III et al. | 5,891,141 A | 4/1999 | Rydell |
| 5,601,601 A | 2/1997 | Tal et al. | 5,891,142 A | 4/1999 | Eggers et al. |
| 5,603,711 A | 2/1997 | Parins et al. | 5,893,863 A | 4/1999 | Yoon |
| 5,603,723 A | 2/1997 | Aranyi et al. | 5,893,875 A | 4/1999 | O'Connor et al. |
| 5,611,798 A | 3/1997 | Eggers | 5,893,877 A | 4/1999 | Gampp, Jr. et al. |
| 5,620,453 A | 4/1997 | Nallakrishnan | 5,902,301 A | 5/1999 | Olig |
| 5,624,452 A | 4/1997 | Yates | 5,906,630 A | 5/1999 | Anderhub et al. |
| 5,626,578 A | 5/1997 | Tihon | 5,908,420 A | 6/1999 | Parins et al. |
| 5,626,609 A | 5/1997 | Zvenyatsky et al. | 5,908,432 A | 6/1999 | Pan |
| 5,630,833 A | 5/1997 | Katsaros et al. | 5,911,719 A | 6/1999 | Eggers |
| 5,637,110 A | 6/1997 | Pennybacker et al. | 5,913,874 A | 6/1999 | Berns et al. |
| 5,638,003 A | 6/1997 | Hall | 5,921,984 A | 7/1999 | Sutcu et al. |
| 5,643,294 A | 7/1997 | Tovey et al. | 5,925,043 A | 7/1999 | Kumar et al. |
| 5,647,869 A | 7/1997 | Goble et al. | 5,935,126 A | 8/1999 | Riza |
| 5,647,871 A | 7/1997 | Levine et al. | 5,944,718 A | 8/1999 | Dafforn et al. |
| 5,649,959 A | 7/1997 | Hannam et al. | 5,951,549 A | 9/1999 | Richardson et al. |
| 5,658,281 A | 8/1997 | Heard | 5,954,720 A | 9/1999 | Wilson et al. |
| 5,662,667 A | 9/1997 | Knodel | 5,957,923 A | 9/1999 | Hahnen et al. |
| 5,665,100 A | 9/1997 | Yoon | 5,960,544 A | 10/1999 | Beyers |
| 5,667,526 A | 9/1997 | Levin | 5,961,514 A | 10/1999 | Long et al. |
| 5,674,220 A | 10/1997 | Fox et al. | 5,964,758 A | 10/1999 | Dresden |
| 5,681,282 A | 10/1997 | Eggers et al. | 5,976,132 A | 11/1999 | Morris |
| 5,688,270 A | 11/1997 | Yates et al. | 5,984,939 A | 11/1999 | Yoon |
| 5,693,051 A | 12/1997 | Schulze et al. | 5,989,277 A | 11/1999 | LeMaire, III et al. |
| 5,695,522 A | 12/1997 | LeMaire, III et al. | 5,997,565 A | 12/1999 | Inoue |
| 5,700,261 A | 12/1997 | Brinkerhoff | 6,004,335 A | 12/1999 | Vaitekunas et al. |
| 5,702,390 A | 12/1997 | Austin et al. | 6,010,516 A | 1/2000 | Hulka |
| 5,707,369 A | 1/1998 | Vaitekunas et al. | 6,024,741 A | 2/2000 | Williamson et al. |
| 5,709,680 A | 1/1998 | Yates et al. | 6,024,744 A | 2/2000 | Kese et al. |
| 5,716,366 A | 2/1998 | Yates | 6,030,384 A | 2/2000 | Nezhat |
| 5,720,744 A | 2/1998 | Eggleston et al. | 6,033,399 A | 3/2000 | Gines |
| 5,722,421 A | 3/1998 | Francese et al. | 6,039,733 A | 3/2000 | Buysse et al. |
| 5,725,536 A | 3/1998 | Oberlin et al. | 6,041,679 A | 3/2000 | Slater et al. |
| 5,727,428 A | 3/1998 | LeMaire, III et al. | 6,050,996 A * | 4/2000 | Schmaltz et al. ............... 606/51 |
| 5,735,848 A | 4/1998 | Yates et al. | 6,053,914 A | 4/2000 | Eggers et al. |
| 5,743,906 A | 4/1998 | Parins et al. | 6,053,933 A | 4/2000 | Balazs et al. |
| 5,755,717 A | 5/1998 | Yates et al. | D424,694 S | 5/2000 | Tetzlaff et al. |
| 5,766,130 A | 6/1998 | Selmonosky | D425,201 S | 5/2000 | Tetzlaff et al. |
| 5,766,166 A | 6/1998 | Hooven | 6,059,782 A | 5/2000 | Novak et al. |
| 5,766,170 A | 6/1998 | Eggers | 6,074,386 A | 6/2000 | Goble et al. |
| 5,769,849 A | 6/1998 | Eggers | RE36,795 E | 7/2000 | Rydell |
| 5,772,655 A | 6/1998 | Bauer et al. | 6,083,223 A | 7/2000 | Baker |
| 5,772,670 A | 6/1998 | Brosa | 6,086,586 A | 7/2000 | Hooven |
| 5,776,128 A | 7/1998 | Eggers | 6,090,107 A | 7/2000 | Borgmeier et al. |
| 5,776,130 A | 7/1998 | Buysse et al. | 6,096,037 A | 8/2000 | Mulier et al. |
| 5,779,701 A | 7/1998 | McBrayer et al. | 6,099,550 A | 8/2000 | Yoon |
| H1745 H | 8/1998 | Paraschac | 6,102,909 A | 8/2000 | Chen et al. |
| 5,792,137 A | 8/1998 | Carr et al. | 6,110,171 A | 8/2000 | Rydell |
| 5,792,177 A | 8/1998 | Kaseda | 6,113,596 A | 9/2000 | Hooven et al. |
| 5,797,927 A | 8/1998 | Yoon | 6,113,598 A | 9/2000 | Baker |
| 5,797,938 A | 8/1998 | Paraschac et al. | 6,117,158 A | 9/2000 | Measamer et al. |
| 5,797,941 A | 8/1998 | Schulze et al. | 6,123,701 A | 9/2000 | Nezhat |
| 5,797,958 A | 8/1998 | Yoon | H1904 H | 10/2000 | Yates et al. |
| 5,800,449 A | 9/1998 | Wales | 6,126,658 A | 10/2000 | Baker |
| 5,807,393 A | 9/1998 | Williamson, IV et al. | 6,152,923 A | 11/2000 | Ryan |
| 5,810,808 A | 9/1998 | Eggers | 6,162,220 A | 12/2000 | Nezhat |
| 5,810,811 A | 9/1998 | Yates et al. | 6,174,309 B1 | 1/2001 | Wrublewski et al. |
| 5,810,877 A | 9/1998 | Roth et al. | 6,179,834 B1 | 1/2001 | Buysse et al. |
| 5,814,043 A | 9/1998 | Shapeton | 6,179,837 B1 | 1/2001 | Hooven |
| 5,817,083 A | 10/1998 | Williamson IV et al. | 6,183,467 B1 | 2/2001 | Shapeton et al. |
| 5,820,630 A | 10/1998 | Lind | 6,187,003 B1 | 2/2001 | Buysse et al. |

| | | | |
|---|---|---|---|
| 6,190,386 B1 | 2/2001 | Rydell | |
| 6,193,718 B1 | 2/2001 | Kortenbach et al. | |
| 6,206,876 B1 | 3/2001 | Levine et al. | |
| 6,206,877 B1 | 3/2001 | Kese et al. | |
| 6,217,602 B1 | 4/2001 | Redmon | |
| 6,221,039 B1 | 4/2001 | Durgin et al. | |
| 6,224,593 B1 | 5/2001 | Ryan et al. | |
| 6,228,080 B1 | 5/2001 | Gines | |
| 6,228,083 B1 | 5/2001 | Lands et al. | |
| 6,267,761 B1 | 7/2001 | Ryan | |
| 6,270,497 B1 | 8/2001 | Sekino et al. | |
| 6,270,508 B1 | 8/2001 | Klieman et al. | |
| 6,273,887 B1 | 8/2001 | Yamauchi et al. | |
| 6,277,117 B1 | 8/2001 | Tetzlaff et al. | |
| 6,280,458 B1 | 8/2001 | Boche et al. | |
| 6,283,961 B1 | 9/2001 | Underwood et al. | |
| D449,886 S | 10/2001 | Tetzlaff et al. | |
| 6,302,424 B1 | 10/2001 | Gisinger et al. | |
| 6,319,451 B1 | 11/2001 | Brune | |
| 6,322,561 B1 | 11/2001 | Eggers et al. | |
| 6,325,795 B1 * | 12/2001 | Lindemann et al. | 606/32 |
| 6,334,860 B1 | 1/2002 | Dorn | |
| 6,334,861 B1 * | 1/2002 | Chandler et al. | 606/50 |
| 6,345,532 B1 | 2/2002 | Coudray et al. | |
| 6,350,264 B1 | 2/2002 | Hooven | |
| 6,352,536 B1 | 3/2002 | Buysse et al. | |
| 6,358,249 B1 | 3/2002 | Chen et al. | |
| 6,358,268 B1 | 3/2002 | Hunt et al. | |
| D457,958 S | 5/2002 | Dycus et al. | |
| D457,959 S | 5/2002 | Tetzlaff et al. | |
| 6,387,094 B1 | 5/2002 | Eitenmuller | |
| 6,391,035 B1 | 5/2002 | Appleby et al. | |
| 6,398,779 B1 | 6/2002 | Buysse et al. | |
| 6,402,747 B1 | 6/2002 | Lindemann et al. | |
| 6,409,728 B1 | 6/2002 | Ehr et al. | |
| H2037 H | 7/2002 | Yates et al. | |
| 6,419,675 B1 | 7/2002 | Gallo, Sr. | |
| 6,425,896 B1 | 7/2002 | Baltschun et al. | |
| 6,440,144 B1 | 8/2002 | Bacher | |
| 6,443,952 B1 | 9/2002 | Mulier et al. | |
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 * | 10/2002 | Morgan et al. | 606/34 |
| 6,464,701 B1 | 10/2002 | Hooven et al. | |
| 6,464,702 B2 | 10/2002 | Schulze et al. | |
| 6,464,704 B2 | 10/2002 | Schmaltz et al. | |
| 6,500,176 B1 | 12/2002 | Truckai et al. | |
| 6,511,480 B1 * | 1/2003 | Tetzlaff et al. | 606/51 |
| 6,514,252 B2 | 2/2003 | Nezhat et al. | |
| 6,527,771 B1 | 3/2003 | Weadock et al. | |
| 6,558,385 B1 | 5/2003 | McClurken et al. | |
| 6,562,037 B2 | 5/2003 | Paton et al. | |
| 6,585,735 B1 | 7/2003 | Frazier et al. | |
| 6,602,252 B2 | 8/2003 | Mollenauer | |
| 6,616,658 B2 | 9/2003 | Ineson | |
| 6,616,661 B2 | 9/2003 | Wellman et al. | |
| 6,620,161 B2 | 9/2003 | Schulze et al. | |
| 6,626,901 B1 | 9/2003 | Treat et al. | |
| 6,641,595 B1 | 11/2003 | Moran et al. | |
| 6,652,514 B2 | 11/2003 | Ellman et al. | |
| 6,652,521 B2 | 11/2003 | Schulze | |
| 6,656,177 B2 | 12/2003 | Truckai et al. | |
| 6,660,072 B2 | 12/2003 | Chatterjee | |
| 6,669,696 B2 | 12/2003 | Bacher et al. | |
| 6,676,660 B2 | 1/2004 | Wampler et al. | |
| 6,679,882 B1 | 1/2004 | Kornerup | |
| 6,682,527 B2 | 1/2004 | Strul | |
| 6,682,528 B2 | 1/2004 | Frazier et al. | |
| 6,685,724 B1 | 2/2004 | Haluck | |
| 6,689,131 B2 | 2/2004 | McClurken | |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |

| | | |
|---|---|---|
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0026189 A1* | 2/2002 | Wayne et al. .................. 606/42 |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0225288 A1 | 11/2004 | Buysse et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1* | 6/2005 | Moses et al. ................... 606/51 |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |

| | | | |
|---|---|---|---|
| 2007/0179499 A1 | 8/2007 | Garrison | |
| 2007/0203485 A1 | 8/2007 | Keppel | |
| 2007/0213706 A1 | 9/2007 | Dumbauld et al. | |
| 2007/0213707 A1 | 9/2007 | Dumbauld et al. | |
| 2007/0213708 A1 | 9/2007 | Dumbauld et al. | |
| 2007/0213712 A1 | 9/2007 | Buysse et al. | |
| 2007/0255279 A1 | 11/2007 | Buysse et al. | |
| 2007/0260235 A1 | 11/2007 | Podhajsky | |
| 2007/0260238 A1 | 11/2007 | Guerra | |
| 2007/0260241 A1 | 11/2007 | Dalla Betta et al. | |
| 2007/0260242 A1 | 11/2007 | Dycus et al. | |
| 2007/0265616 A1 | 11/2007 | Couture et al. | |
| 2008/0004616 A1 | 1/2008 | Patrick | |
| 2008/0009860 A1 | 1/2008 | Odom | |
| 2008/0015575 A1 | 1/2008 | Odom et al. | |
| 2008/0021450 A1 | 1/2008 | Couture | |
| 2008/0033428 A1 | 2/2008 | Artale et al. | |
| 2008/0039835 A1 | 2/2008 | Johnson et al. | |
| 2008/0045947 A1 | 2/2008 | Johnson et al. | |
| 2008/0058802 A1 | 3/2008 | Couture et al. | |
| 2008/0082100 A1 | 4/2008 | Orton et al. | |

FOREIGN PATENT DOCUMENTS

| | | |
|---|---|---|
| DE | 2415263 | 10/1975 |
| DE | 2627679 | 1/1977 |
| DE | 8712328 | 3/1988 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 518230 A1 | 12/1992 |
| EP | 541 930 B1 | 5/1993 |
| EP | 0572131 | 12/1993 |
| EP | 584787 A1 | 3/1994 |
| EP | 0589453 A2 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1645238 A1 | 4/2006 |
| EP | 1645240 A2 | 4/2006 |
| EP | 1707143 A1 | 10/2006 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO89/00757 | 1/1989 |
| WO | WO 92/04873 | 4/1992 |
| WO | WO 92/06642 | 4/1992 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO00/24331 | 5/2000 |
| WO | WO 00/24331 | 5/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO02/07627 | 1/2002 |
| WO | WO 02/067798 A1 | 9/2002 |
| WO | WO 02/080783 | 10/2002 |
| WO | WO02/080783 | 10/2002 |
| WO | WO 02/080784 | 10/2002 |
| WO | WO02/080784 | 10/2002 |
| WO | WO 02/080785 | 10/2002 |
| WO | WO02/080785 | 10/2002 |
| WO | WO 02/080786 | 10/2002 |
| WO | WO02/080786 | 10/2002 |
| WO | WO 02/080793 | 10/2002 |
| WO | WO02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |

| | | |
|---|---|---|
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO2005/004735 | 1/2005 |
| WO | WP 2005/004734 A1 | 1/2005 |
| WO | WO 2005/110264 | 11/2005 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J. Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson at al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.

Crawford at al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell at al., "Comparison of theGyrus PlasmaKinetic Sealer and the Valleylab LigaSure Device in the Hemostasis of Small, Medium, and Large-Sized Arteries".
Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Seating Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report-extended-EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report-Extended EP 07 009029.5 dated Jul. 12, 2007.
Int'l Search Report EP 07 009321.6 dated Aug. 17, 2007.

* cited by examiner

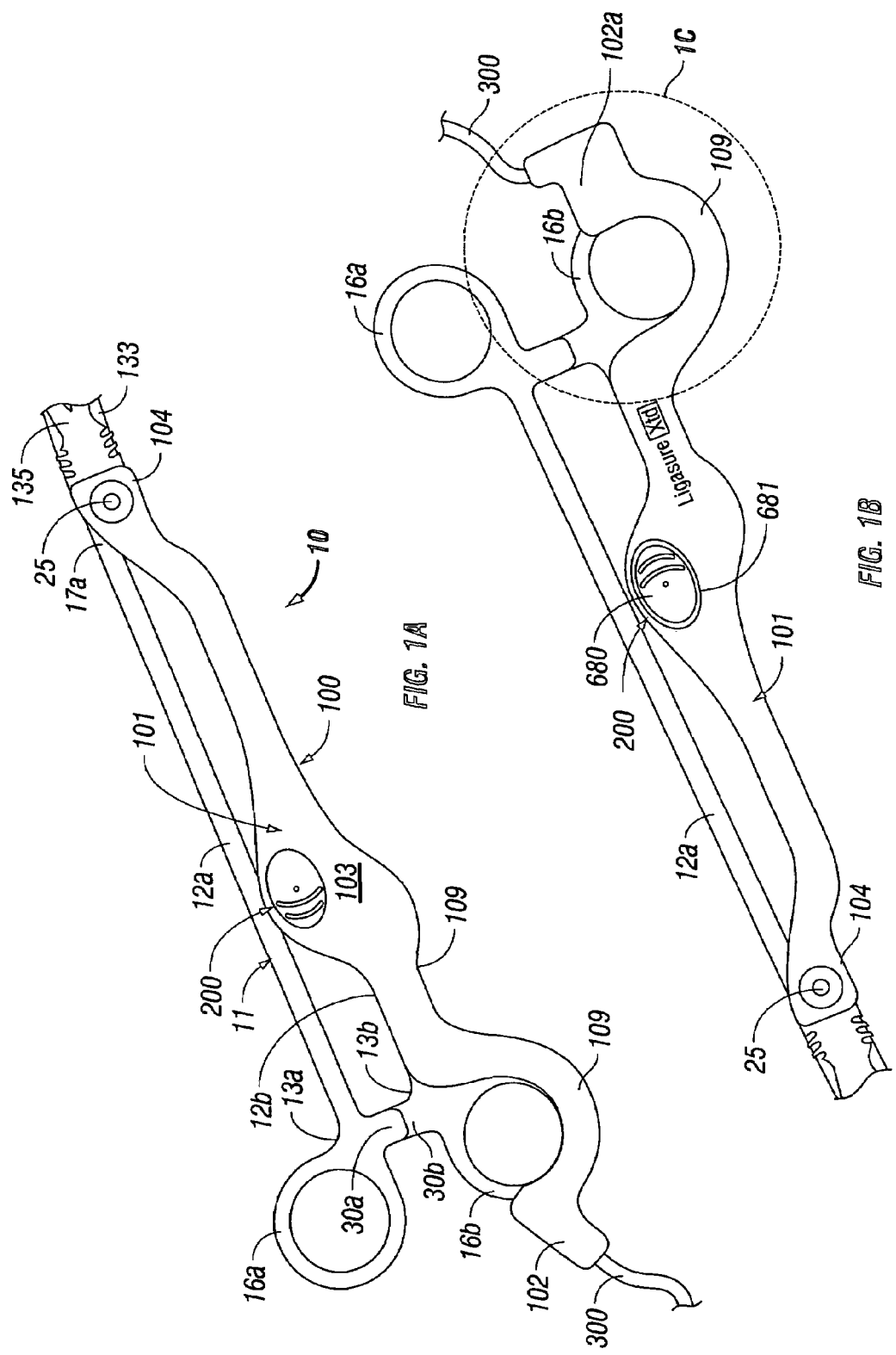

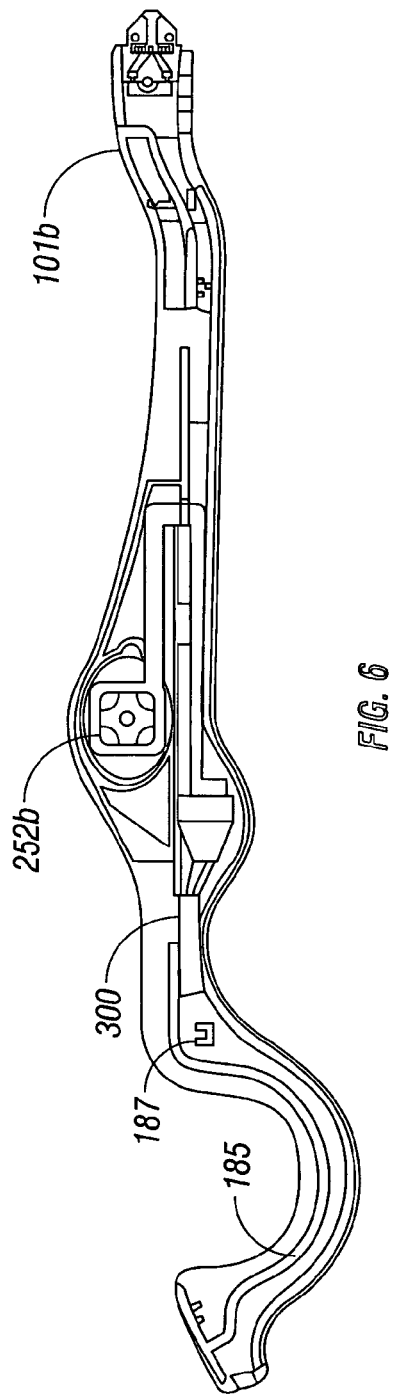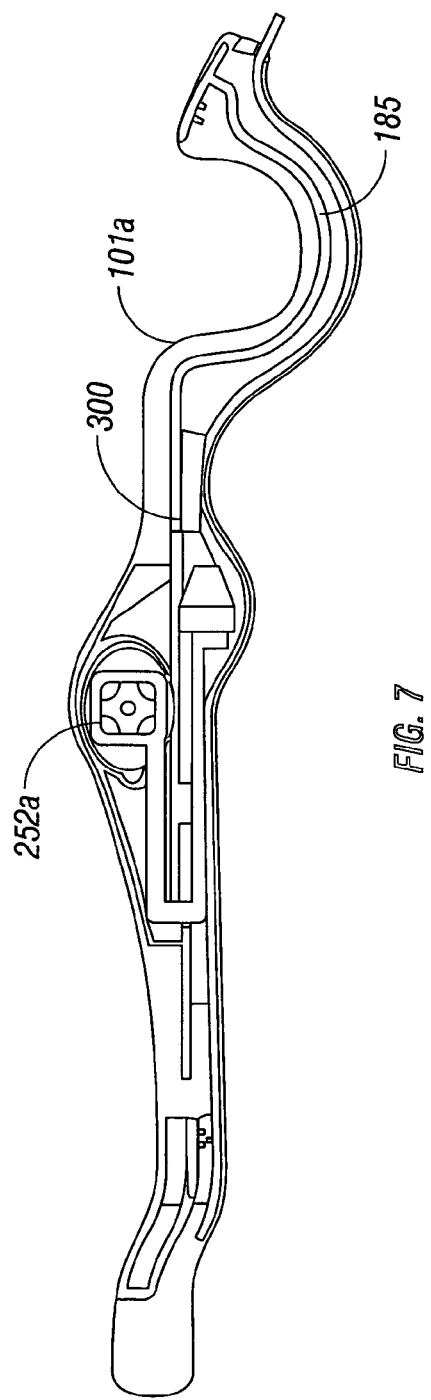

OPEN VESSEL SEALING FORCEPS DISPOSABLE HANDSWITCH

BACKGROUND

The present disclosure relates to electrosurgical forceps used for open surgical procedures. More particularly, the present disclosure relates to an open bipolar forceps having a disposable handswitch and electrode assembly for sealing vessels and vascular tissue.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to affect hemostasis by heating the tissue and blood vessels to coagulate, cauterize, cut and/or seal tissue.

Bipolar electrosurgical forceps utilize two generally opposing electrodes which are disposed on the inner opposing surfaces of end effectors and which are both electrically coupled to an electrosurgical generator. Each electrode is charged to a different electric potential. Since tissue is a conductor of electrical energy, when the effectors are utilized to clamp or grasp tissue therebetween, the electrical energy can be selectively transferred through the tissue.

The process of coagulating small vessels is fundamentally different than vessel sealing. For the purposes herein the term coagulation is defined as a process of desiccating tissue wherein the tissue cells are ruptured and dried. Vessel sealing is defined as the process of liquefying the collagen in the tissue so that it cross-links and reforms into a fused mass. Thus, coagulation of small vessels is sufficient to close them, however, larger vessels need to be sealed to assure permanent closure.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles.

SUMMARY

The present disclosure relates to a removable handswitch and electrode assembly for use with a forceps having opposing end effectors and a handle for effecting relative movement of the end effectors with respect to one another. The removable handswitch and electrode assembly includes a housing having at least one portion which removably engages at least a portion of a mechanical forceps and a handswitch assembly disposed on the housing. A pair of electrodes is included which removably engage a distal end of the mechanical forceps such that the electrodes reside in opposing relation to one another. At least one electrode is adapted to connect to an electrosurgical generator either independently or through the handswitch assembly. At least one stop member is operatively associated with the electrodes and controls the distance between the opposing electrodes to affect a tissue seal. In particular embodiments, the stop member is proximal to the electrodes or on the tissue engaging surfaces of one or more electrodes.

In one embodiment, the handswitch assembly includes at least one activation button disposed on one side of the housing which operatively connects to a flexible circuit board to control the activation of the electrodes. In yet other envisioned embodiments, two independently activatable activation buttons are included on either side of the housing which operatively connect to a flexible circuit board to control the activation of the electrodes. The flexible circuit board is preferably dimensioned to span between two housing halves prior to the housing being assembled. The flexible circuit board includes at least one dome switch which cooperates with the activation button to activate the electrodes. In one embodiment according to the present disclosure, the dome switch and the flexible circuit board are securely supported atop one or more backer plates by one or more mechanical interfaces. The flexible circuit board is configured to wrap around the backer plate(s) and fit within the housing.

The present disclosure also relates to a removable handswitch and electrode assembly for use with a forceps which includes a housing having at least one portion which removably engages at least a portion of a mechanical forceps and a handswitch assembly disposed on the housing adapted to connect to an electrosurgical generator. The handswitch assembly includes a flexible circuit board having at least one portion thereof which operatively communicates with an activation button to control the activation of a pair of electrodes. The electrodes are removably engageable with a distal end of the mechanical forceps such that the electrodes reside in opposing relation to one another.

In one embodiment, the activation button includes a rocker pivot at one end thereof which allows the activation button to pivot into operative communication with the flexible circuit board. In yet another embodiment, a guidance tab is included at one end of the activation button which facilitates alignment and assembly of the activation button atop the flexible circuit board and within the housing.

The present disclosure also relates to a removable handswitch and electrode assembly which includes a housing having at least one portion which removably engages at least a portion of a mechanical forceps and a pair of electrodes which removably engage a distal end of the mechanical forceps such that the electrodes reside in opposing relation to one another. Each electrode is adapted to connect to an electrosurgical generator either independently or though a handswitch assembly which includes a flexible circuit board. The flexible circuit board includes at least one portion which operatively communicates with at least one activation button to control the activation of the pair of electrodes. The activation button (s) is disposed in a recess defined in a side of the housing.

BRIEF DESCRIPTION OF THE DRAWINGS

Various embodiments of the subject instrument are described herein with reference to the drawings wherein:

FIG. 1A is a side view of an open bipolar forceps according to the present disclosure including a disposable handswitch and electrode assembly attached thereto;

FIG. 1B is a side view of an alternate embodiment of an open bipolar forceps according to the present disclosure including a disposable handswitch and electrode assembly with an ergonomically-enhanced proximal end;

FIG. 6 is an internal side view of the handswitch and disposable electrode assembly;

FIG. 7 is an internal side view of the handswitch and disposable electrode assembly showing the routing of an electrical wire therethrough.

DETAILED DESCRIPTION

Figure 1C:
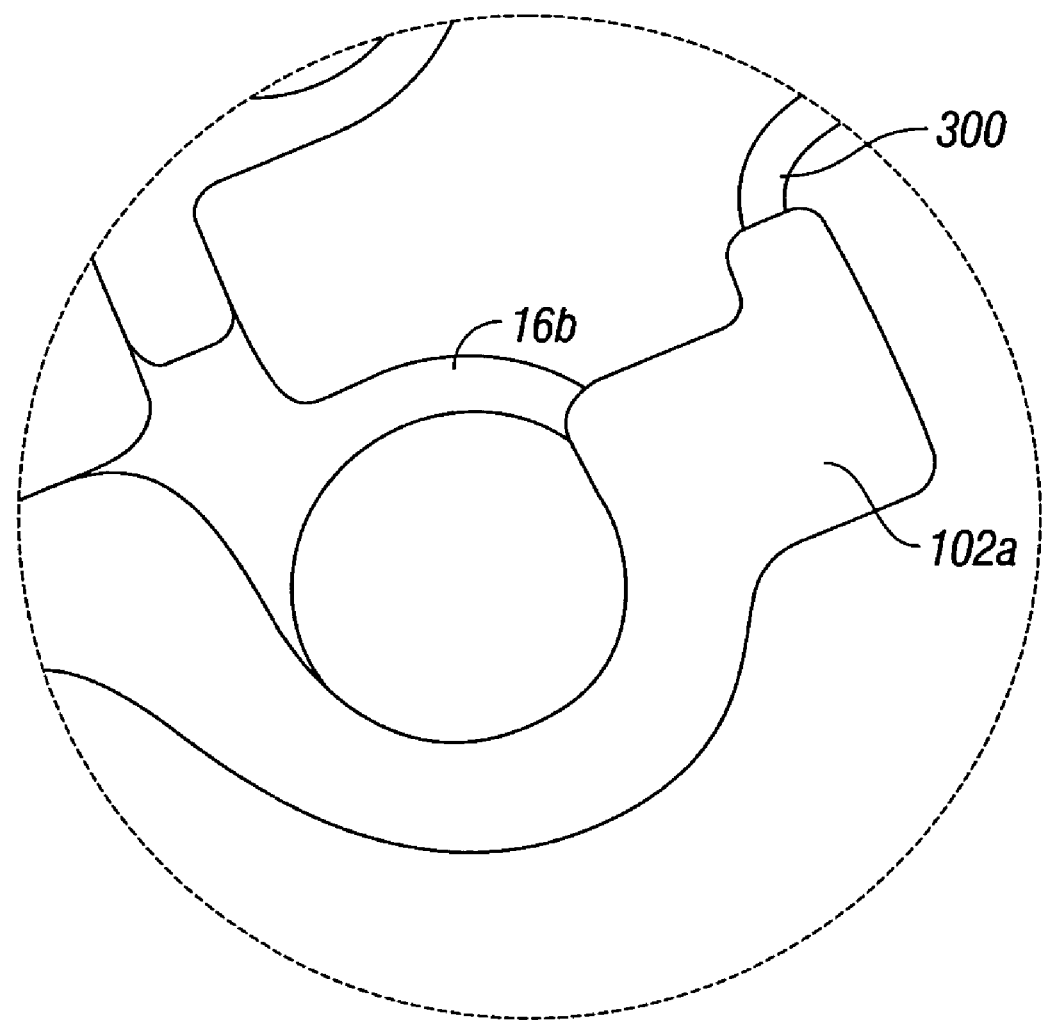
FIG. 1C is an enlarged view of the area of detail of FIG. 1B.

Referring now to FIGS. 1A-1C, a bipolar forceps 10 for use with open surgical procedures includes a mechanical forceps 11 and a disposable handswitch and electrode assembly 100. In the drawings and in the description which follows, the term "proximal", as is traditional, will refer to the end of the forceps 10 which is closer to the user, while the term "distal" will refer to the end which is further from the user.

Mechanical forceps 11 includes first and second elongated shafts 12a and 12b, respectively. Shafts 12a and 12b each include a proximal end 13a and 13b and a distal end 17a and 17b (See FIG. 2A), respectively. Each proximal end 13a, 13b of each shaft portion 12a, 12b includes a handle member 16a and 16b attached thereto to allow a user to effect movement of at least one of the shaft portions 12a and 12b relative to one another. Extending from the distal end 17a and 17b of each shaft portion 12a and 12b are end effectors 22a and 22b, respectively. The end effectors 22a and 22b are movable relative to one another in response to movement of handle members 16a and 16b. Shaft members 12a and 12b are designed to transmit a particular desired force to the end effectors 22a and 22b when clamped. In particular, since the shaft members 12a and 12b effectively act together in a spring-like manner (i.e., bending that behaves like a spring), the length, width, height and deflection of the shaft members 12a and 12b will directly effect the overall transmitted force imposed on opposing end effectors 22a and 22b. Preferably, end effectors 22a and 22b are more rigid than the shaft members 12a and 12b and the strain energy stored in the shaft members 12a and 12b provides a constant closure force therebetween.

Shaft portions 12a and 12b are affixed to one another at a pivot 25 proximate the end effectors 22a and 22b such that movement of the handles 16a and 16b impart movement of the end effectors 22a and 22b from an open position wherein the end effectors 22a and 22b are disposed in spaced relation relative to one another to a clamping or closed position wherein the end effectors 22a and 22b cooperate to grasp tissue therebetween.

Figure 2A:
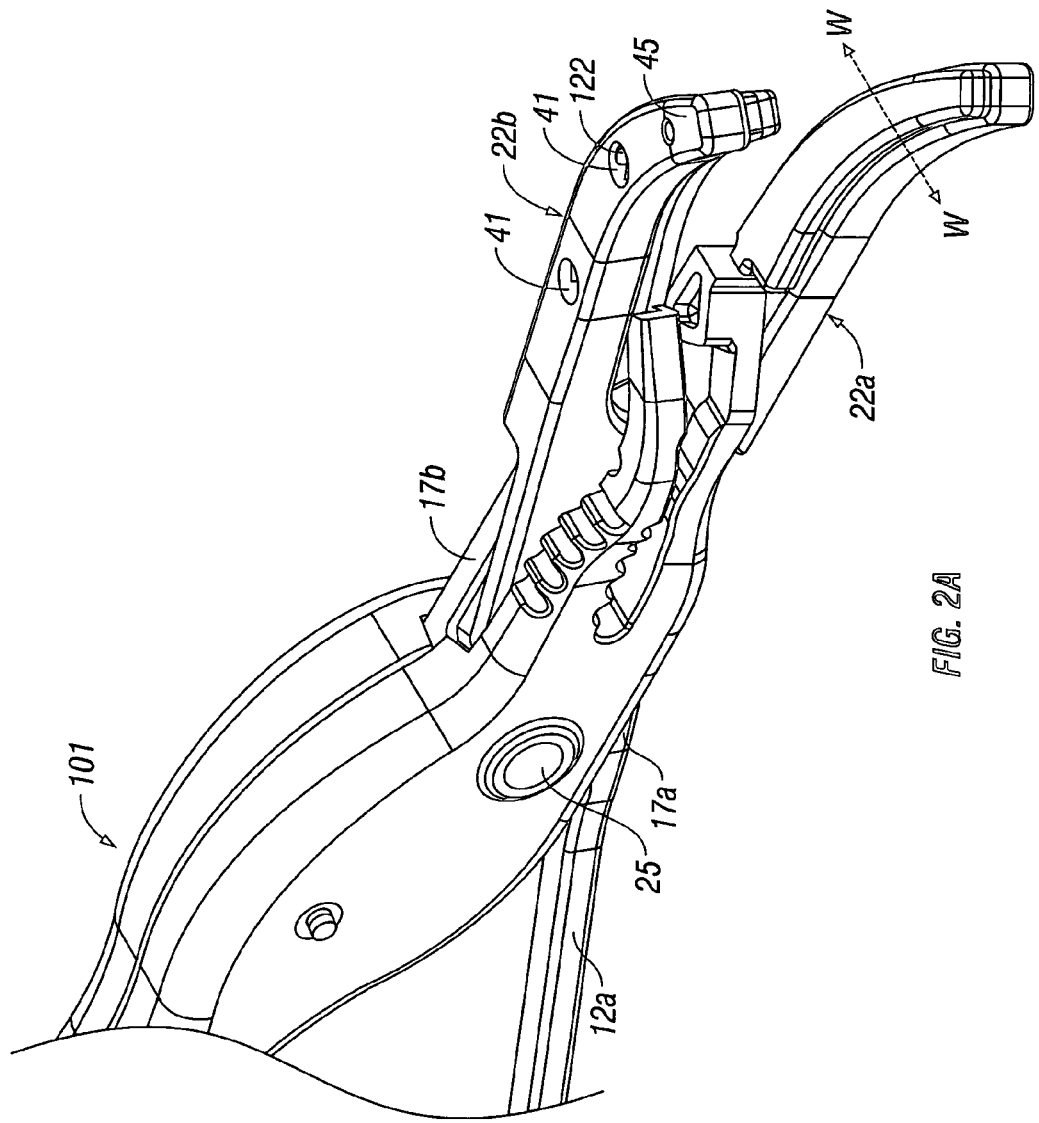
FIG. 2A is an enlarged, perspective view of the distal end of the handswitch and disposable electrode assembly shown attached to a distal end of a forceps.
Figure 2B:
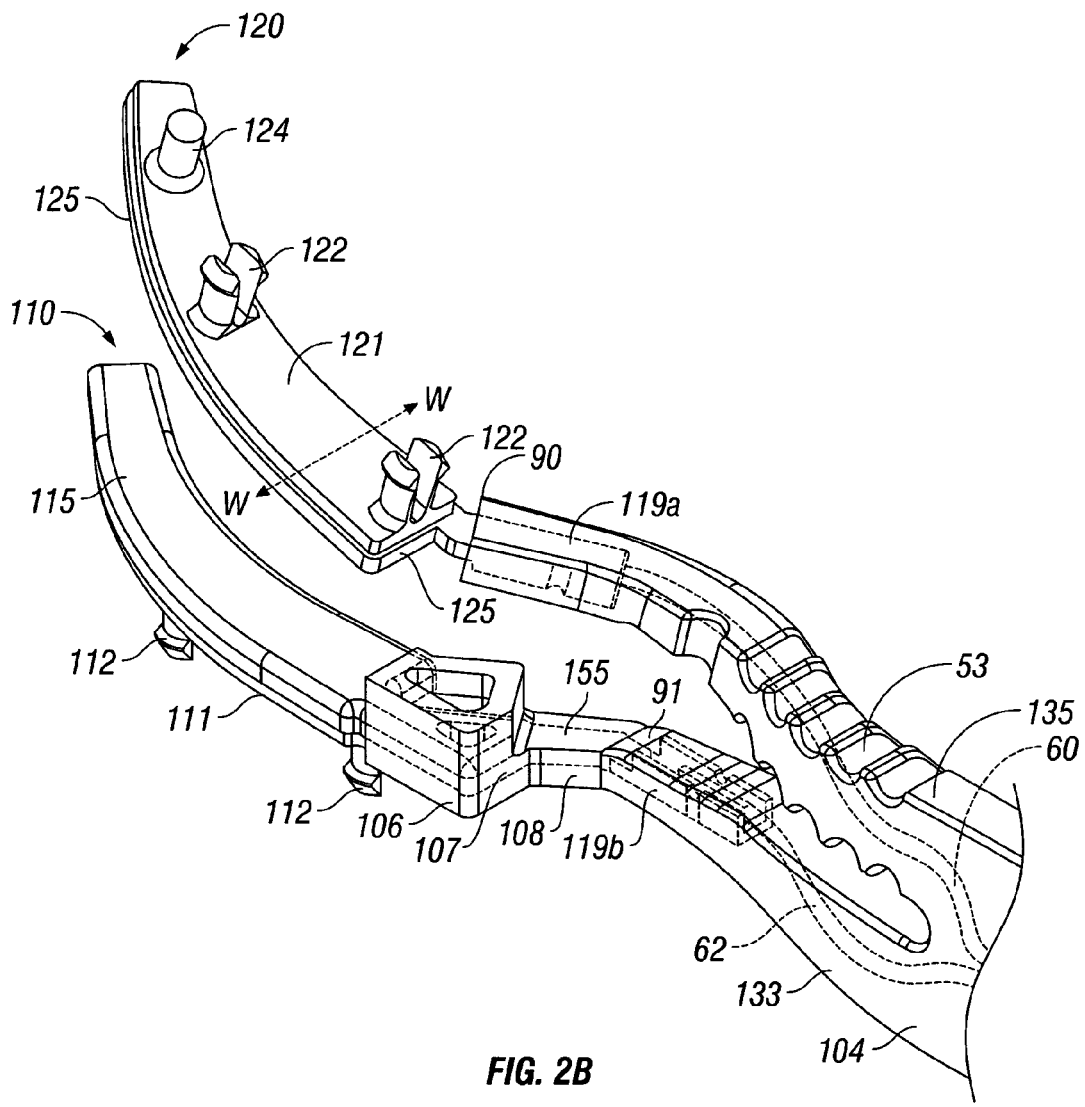
FIG. 2B is an enlarged, perspective view of the distal end of the handswitch and disposable electrode assembly shown separated from the forceps.

As best seen in FIG. 2A, end effector 22b includes an engagement surface 45 having a plurality of mechanical interfaces 41 disposed thereon which are dimensioned to releasable engage a portion of the disposable handswitch and electrode assembly 100 which will be described in greater detail below. For example, mechanical interfaces 41 may include sockets which are disposed at least partially through engagement surface 45 of end effector 22b and which are dimensioned to receive a complimentary mechanical interface attached to disposable handswitch and electrode assembly 100, e.g., detent 122. While the term socket is used herein, it is contemplated that either a male or female mechanical interfaces may be used depending upon a particular purpose. End effector 22a includes similar mechanical interfaces for engaging the disposable handswitch and electrode assembly 100 to end effector 22a.

Each shaft member 12a and 12b also includes a ratchet portion 30a and 30b that mutually extend inwardly from respective proximal ends 13a and 13b of shaft member 12a and 12b towards the one another in a generally vertically aligned manner such that the inner facing surfaces of each ratchet 30a and 30b interlock to hold a specific, i.e., constant, strain energy in the shaft members 12a and 12b. A design without a ratchet system or similar system would require the user to hold the end effectors together by applying constant force to the handles 16a and 16b which may yield inconsistent results especially when sealing.

As best seen in FIGS. 1A-1C and 2A-2D, disposable handswitch and electrode assembly 100 is designed to work in combination with mechanical forceps 11. Electrode assembly 100 includes housing 101 which has a proximal end 102, a distal end 104 and an elongated shaft plate 103 disposed therebetween. A handle plate 109 is disposed near the proximal end 102 and is sufficiently dimensioned to releasably engage and/or encompass handle 16b of mechanical forceps 11. Likewise, shaft plate 103 is dimensioned to encompass and/or releasably engage shaft 12b and pivot 25 disposed near the distal end 104 of housing 101. Disposable handswitch and electrode assembly 100 is composed of a two mating halves 101a and 101b which are designed to snap fit over mechanical forceps 11. More particularly, a plurality of male or female mechanical interfaces or a combination of mechanical interfaces may be disposed on one half 101a of the housing 101 with mating mechanical interfaces disposed on the other housing half 101b. A one piece housing 101 is also contemplated which mechanically engages the mechanical forceps 11 in a secure fashion.

As best seen with respect to FIGS. 2A-2D, the distal end 104 of disposable handswitch and electrode assembly 100 is bifurcated such that two prong-like members 133 and 135 extend outwardly therefrom to support corresponding electrodes 110 and 120, respectively. More particularly, electrode 120 is affixed at an end 90 of prong 135 and electrode 110 is affixed at an end 91 of prong 133. It is envisioned that the electrodes 110 and 120 can be affixed to the ends 91 and 90 in any known manner such as, e.g., frictional or snap-fit engagement.

A pair of electrical leads or wires 60 and 62 is connected to the electrodes 120 and 110, respectively. Preferably, leads 60 and 62 are bundled together and form a wire bundle 28 which runs from a handswitch assembly 200 through the distal end 104 to respective electrodes 110 and 120.

Figure 2C:
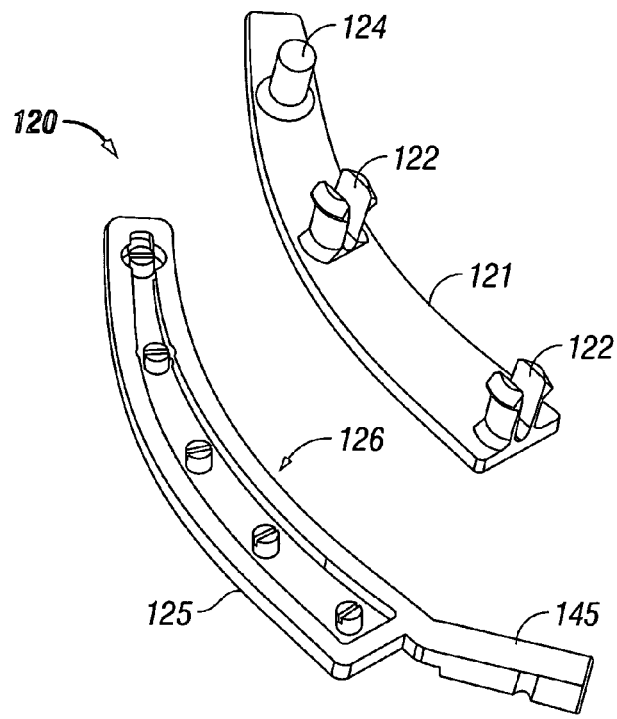
FIG. 2C is a perspective view with parts separated of an upper electrode of the handswitch and disposable electrode assembly of FIG. 2B.

As best seen in FIG. 2C, electrode 120 includes an electrically conductive seal surface 126 and an electrically insulative substrate 121 which are attached to one another by snap-fit engagement or some other method of assembly, e.g., substrate 121 is overmolded to capture the electrically conductive seal surface 126. Substrate 121 may be made from an injection molded plastic material and is shaped to mechanically engage a corresponding socket 41 located in end effector 22b. The substrate 121 not only insulates the electric current but substrate 121 also aligns electrode 120 both of which contribute to the seal quality and consistency. For example, by overmolding the conductive surface 126 to the substrate 121, the alignment and thickness of the electrode 120 can be effectively controlled.

Substrate 121 includes a plurality of bifurcated detents 122 which are shaped to compress during insertion into sockets 41 and expand and releasably engage sockets 41 after insertion. It is envisioned that this snap-fit engagement of the electrode 120 and the end effector 22b will accommodate a broader range of manufacturing tolerances. Substrate 121 may also include one or more alignment or guide pins 124 which mechanically align with a corresponding mechanical interface in end effector 22b.

Conductive seal surface 126 includes a wire crimp 145 designed to engage the distal end 90 of prong 135 of handswitch and electrode assembly 100 and electrically engage a corresponding wire connector affixed to lead 60. Seal surface 126 also includes an opposing tissue-engaging face 125 which is designed to conduct an electrosurgical current to tubular vessels or tissue when held thereagainst.

Figure 2D:
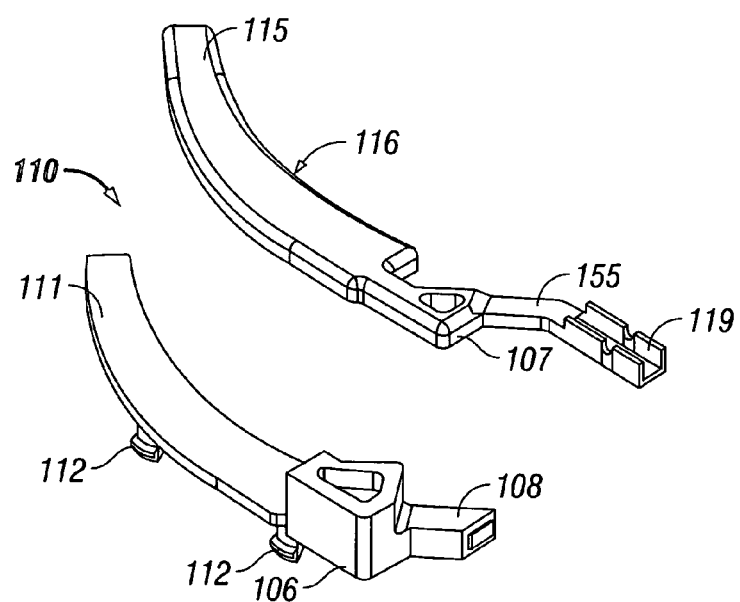
FIG. 2D is a perspective view with parts separated of a lower electrode of the handswitch and disposable electrode assembly of FIG. 2B.

As shown in FIG. 2D, electrode 110 includes similar elements for insulating and conducting electrosurgical current to tissue. More particularly, electrode 110 includes an electrically conductive seal surface 116 and an electrically insulative substrate 111 which are attached to one another by snap-fit engagement or some other method of assembly. Substrate 111 includes a plurality of bifurcated detents 112 and an alignment pin 126 which are dimensioned to engage a corresponding plurality of sockets and aperture (not shown) located in end effector 22a. Conductive seal surface 116 includes an extension 155 having a wire crimp 119 which engages the distal end 91 of prong 133 and electrically engages a corresponding wire connector affixed to lead 62 located in housing 101. Seal surface 116 also includes an opposing face 115 which conducts an electrosurgical current to tissue when held thereagainst. Alternatively, electrodes 110 or 120 can be formed as one piece and include similar components for insulating and conducting electrical energy.

Substrate 111 also includes an extension 108 and a stop member 106 which is designed to engage corresponding extension 155 and an interface 107 located proximal conductive seal surface 116. To assemble electrode 110, stop member 106 and extension 108 are overmolded onto interface 107 and extension 155 of conductive seal 116. After assembly, wire crimp 119 is then inserted into end 91 of prong member 133 and connected to lead 62. In order to assure that the desired gap range is achieved after assembly and that the correct force is applied to seal the tissue, substrate 111 includes at least one stop member, 106, which is designed to restrict and/or regulate movement of the two electrodes 110 and 120 relative to one another.

It is known that as the tissue is compressed and electrosurgical energy is applied to the tissue, the impedance of the tissue decreases as the moisture level decreases. As a result, two mechanical factors play an important role in determining seal thickness and effectiveness, i.e., the pressure applied between opposing faces 115 and 125 and the gap distance between the opposing electrodes 110 and 120. When, the end effectors 22a and 22b closed about tissue, stop member 106 is configured to keep the requisite gap range of about 0.001 inches to about 0.006 inches between opposing sealing surfaces 115 and 125 and more preferably, between about 0.002 inches to about 0.005 inches. The shafts 12a and 12b are preferably designed to provide and the ratchets 30a and 30b are preferably designed to maintain pressure between end effectors 22a and 22b within the range of about 3 kg/cm$^2$ to about 16 kg/cm$^2$.

It is contemplated that one or more stop members (not shown) may be positioned at various points along the disposable handswitch and electrode assembly 100 to achieve the aforedescribed desired gap range and/or one or more stop members can be positioned on other parts of the instrument, e.g., handles 16a, 16b, on sealing surfaces 115 and/or 125, and/or shafts 12a, 12b. The additional stop members may be utilized in connection with stop member 106 or used instead of stop member 106 to regulate the gap distance between opposing electrodes 110 and 120.

At least one of the prong members, e.g., 135, is resilient or includes a flex relief portion 53 which permits movement of the two prong members 135 and 133 and, thus, the two electrodes 120 and 110, relative to one another. The flex relief portions 135 and 133 may be configured to bias the end effectors 22a and 22b in an open position. As seen best in FIG. 2B, the disposable handswitch and electrode assembly 100 is removably attached to the mechanical forceps 11 by initially moving prong 135 towards prong 133 by bending prong 135 at flex relief portion 53. The electrodes 110 and 120 are then slid between opposing end effectors 22a and 22b in their open position such that detents 112 and 122 and guide pins 126 and 124, respectively, are each disposed in alignment with each corresponding mechanical interface (not shown), respectively. When flex relief portion 53 is released, each electrode 110 and 120 is engaged with end effector 22a and 22b, respectively, and the bipolar forceps 10 is now ready for operation.

After the bipolar forceps 10 is used or if the disposable handswitch and electrode assembly 100 is damaged, the electrode assembly 100 can be easily removed and/or replaced by reversing the above attachment procedure and a new electrode assembly 100 can be engaged with the mechanical forceps 11 in the same manner. By making the handswitch and electrode assembly 100 disposable, the electrode assembly 100 is less likely to become damaged since it is only intended for a single use and, therefore, does not require cleaning or sterilization. As a result, the functionality and consistency of the vital sealing components, e.g., the conductive surface 115, 125 and insulating surface 121, 111 will assure a uniform and quality seal.

As mentioned above, the bipolar forceps also includes a handswitch 200 assembly disposed on the housing 101 to permit the user to selectively apply electrosurgical energy as needed to seal tissue grasped between electrodes 110 and 120. Handswitch assembly 200 includes a flexible circuit board (FCB) 250, a backer plate assembly 260 and a pair of activation buttons 280 which all mutually cooperate to allow selective activation of the electrode assembly 100. As can be appreciated, positioning the handswitch assembly 200 on the forceps 10 gives the user more visual and tactile control over the application of electrosurgical energy. These aspects are explained below with respect to the discussion of the handswitch assembly 200 and the electrical connections associated therewith.

Referring back to FIG. 1A, the housing 101 is particularly configured to include various ergonomically-friendly features to enhance the feel and handling of the forceps 10. The particular shape of the contour is designed to integrate smoothly with the hand of the operator thereby reducing operator fatigue and helping to maximize productivity. While keeping the general hemostat design, certain profile features have been added to facilitate handling and ease of use. For example, the handswitch assembly 200 may include a two-button design allowing both left-handed and right-handed operation with the curve of the jaw members facing in a preferred orientation (i.e., facing outwardly). The lower portion of the housing 101 (i.e., the portion opposite the handswitch assembly 200) features a symmetrical protruding sweep 109 that allows placement of an operator's forefinger to give the operator enhanced control during difficult surgical maneuvers (e.g., operating in deep surgical cavities). The contoured design also provides additional surface area for torquing purposes. The particular placement of activation button 280 of the handswitch assembly 200 on housing 101 is designed to limit or reduce finger travel for activation purposes. The internal portion of the lower sweep 109 is configured to house the soldering joint on the terminal connections 265a and 265b of the flexible circuit board 250 and the heat shrink associated therewith.

Figure 3A:
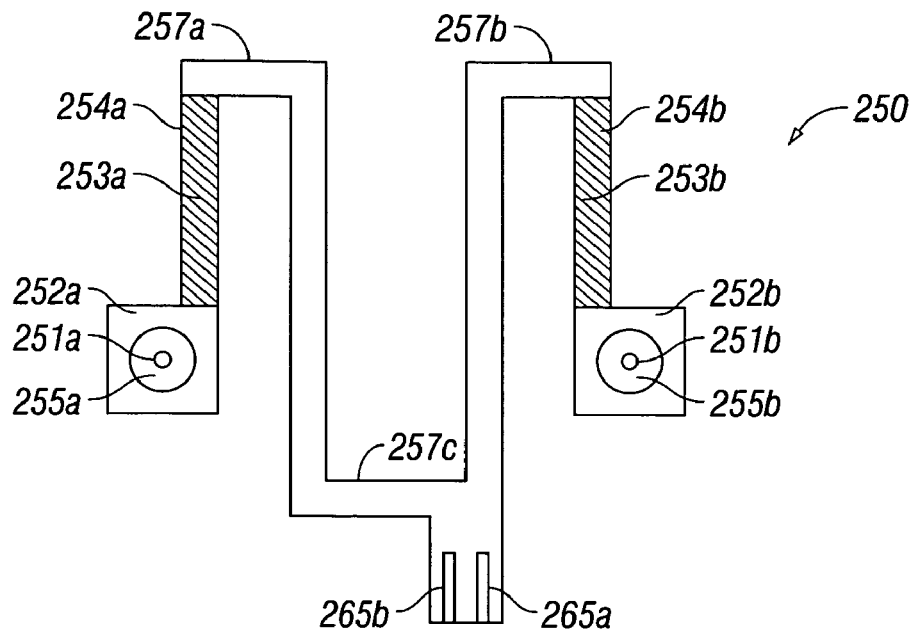
FIG. 3A is a schematic diagram of a flex circuit for use with the handswitch and disposable electrode assembly.
Figure 3C:
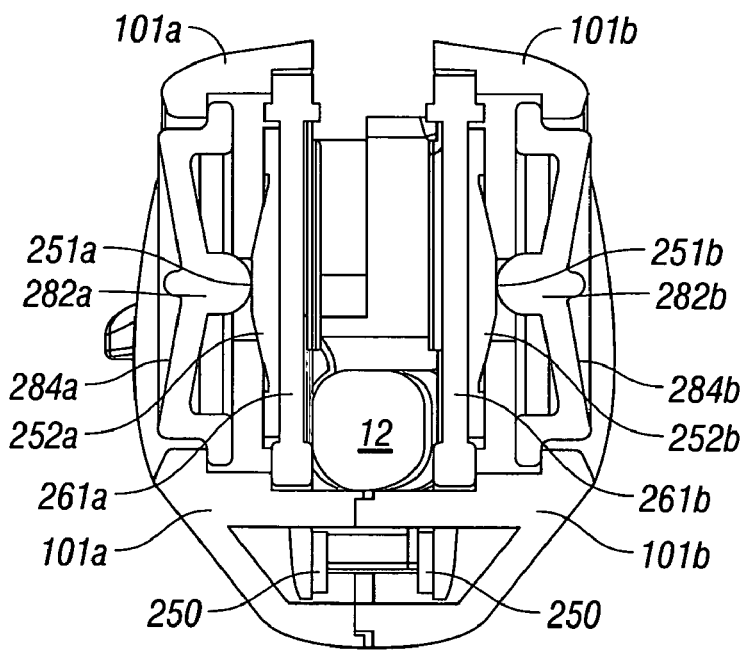
FIG. 3C is a rear cross-section of the handswitch and disposable electrode assembly shown assembled.
Figure 3B:
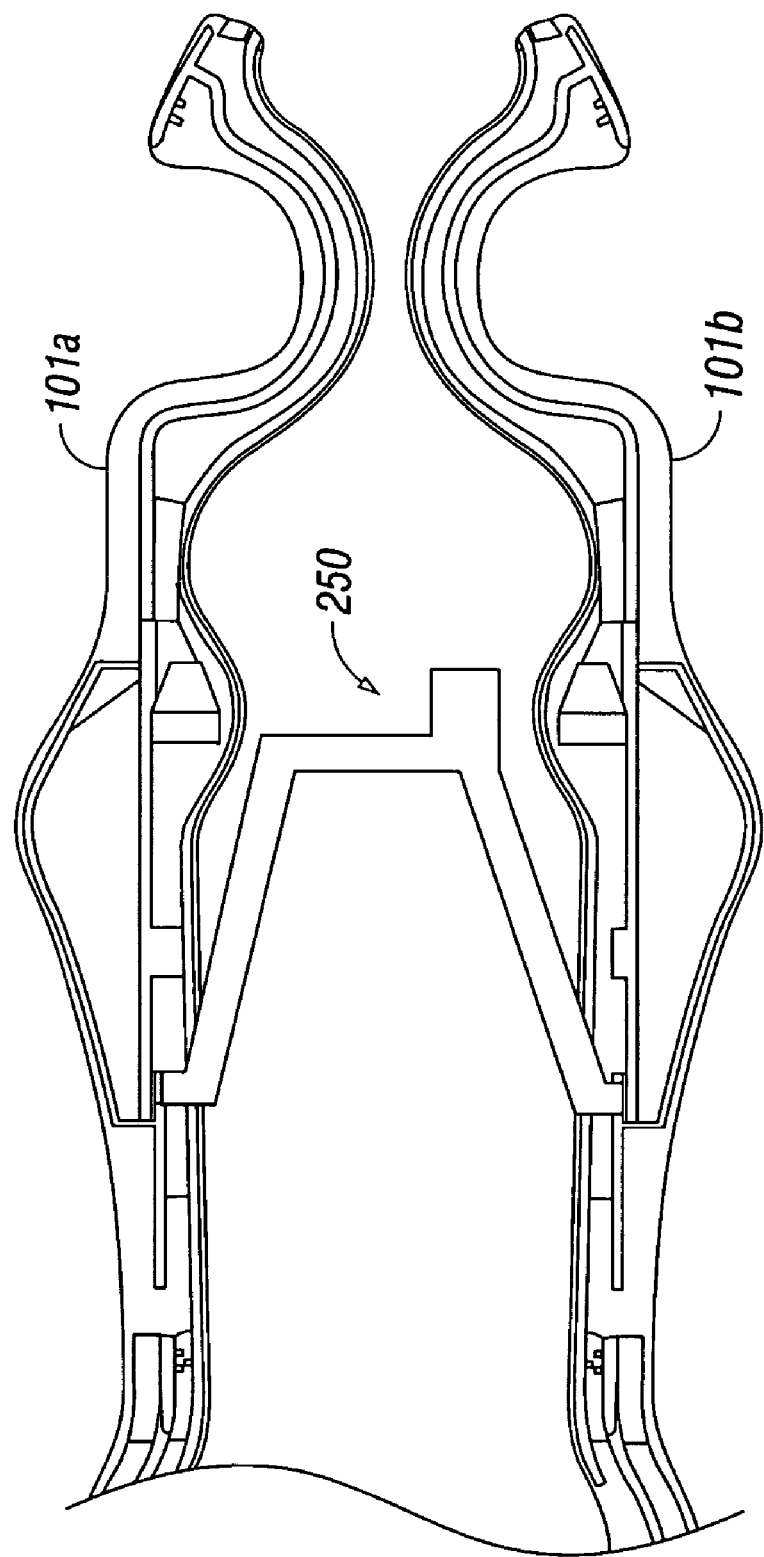
FIG. 3B is a top, perspective view of the disposable handswitch and electrode assembly prior to assembly showing a flex-type circuit bridging between the two electrode assembly body halves.

As best shown in FIGS. 6 and 7, an electrical cable 300 is routed through one or more channels 185 defined in the housing 101 and connects to the FCB 250. One or more pinch points 187 may be included to facilitate routing of the cable 300 during assembly. FIGS. 3A-3C show FCB 250 which includes a set of two dome switches 252a and 252b which are configured to span across the two halves 101a and 101b of housing 101 during assembly. As can be appreciated, using a FCB has many advantages over conventional circuit designs in that the FCB is very thin and has the ability to "flex" and twist without risk of disconnection. Moreover, FCBs are easy to assemble, their internal matrix limits the effects that fluid ingress could cause on the circuit and the lengthy, windy shape creates room to bridge the gap between the two plastic halves of the housing 101. Preferably, FCB 250 is constructed using known photo-masking techniques, wherein a photo-mask is applied to the desired dielectric surfaces of a flexible substrate and no photo-mask is applied to the desired conductive surfaces of the flexible substrate. Other masking techniques are also envisioned for forming FCB 250.

Figure 4:
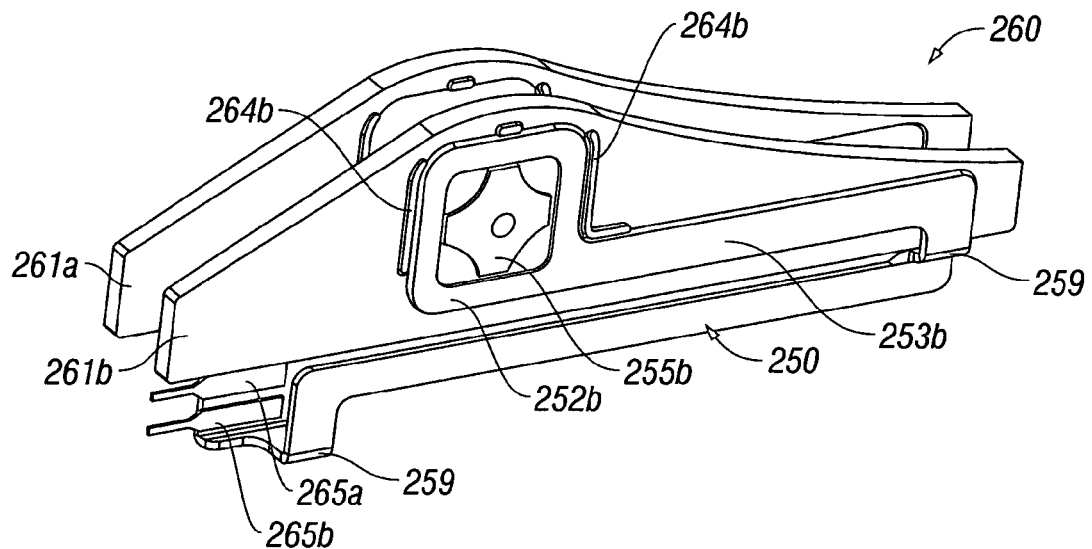
FIG. 4 is an enlarged, partial perspective view of a backer plate which supports the flexible circuit board of FIG. 3A.

FCB 250 also includes a series of leg portions 257a, 257b and 257c and arms 253a and 253b are disposed between the two dome switches 252 which allow the FCB 250 to "flex" as needed during assembly. One or more bend points 259 may also be included between each respective arm and leg portion, e.g., 253a, 257a and 253b, 257b which allow the FCB 250 to wrap around the back plate assembly 260 as shown in FIG. 4. As can be appreciated, configuring the FCB 250 in this fashion has several advantages including facilitating the assembly process of housing 101 and allowing left-handed or right-handed activation as described in more detail below.

FCB 250 also includes at least one resistor which is configured to span between the two dome switches 252a and 252b. For example and as shown in FIG. 3A, each arm 253a and 253b of the dome switches 252a and 252b includes a resistor 254a and 254b, respectively, which are each configured to limit current passing though each dome switch 252a and 252b, respectively. It is envisioned that only one resistor would be necessarily needed if placed before the traces of the FCB 250 split into respective leg portions 257a and 257b. Terminal connections 265a and 265b are provided between the two dome switches 252a and 252b which connect to leads 60 and 62 leading from handswitch assembly 200 to electrodes 110 and 120. It is envisioned that locating the terminal connections 265a and 265b to the proximal portion of the housing 101 isolates the heat shrink and allows for more room within the housing 101. The terminal connections 265a and 265b are preferably offset so that the crimped terminals and corresponding wire connections from leads 60 and 62 will remain flat when the FCB 250 is wrapped to fit into housing 101.

Dome switches 252a and 252b typically include a raised portion or so-called "snap dome" 255a and 255b, respectively, mounted thereto. When one of the snap domes, e.g., 255a, is depressed, the snap dome 255a completes the electrical circuit within the FCB 250. A snap dome-type switch is typically made of a suitable metal or conductive material and configured so that when depressed, a predetermined range of motion is evident to the surgeon (tactile feedback) through a snap phase of closing the electrical circuit. The surgeon develops a tactile "feel" through the range of motion and during activation of the switch when depressed and deflected over the center position. Typically, a snap dome switch includes a dielectric outer layer such as activation button 280 which protects the surgeon from electrical shock during use and reduces the chances of contaminating the switch with surgical fluids.

When mounted atop FCB 250, a conductive apex or central region 251a and 251b, respectively of the snap dome 255a, 255b resides in vertical registration over a contact portion on FCB 250 such that upon depression, snap dome 255a, 255b deflects downwardly to a point where the conductive apex 251a, 251b passes parallel and inverts into contact with the FCB 250. As can be appreciated, the point of inversion as well as the additional range of travel of the membrane provides an enhanced level of tactile feedback to the user thus enabling the user to more readily ascertain the "active" position of the switch. Moreover, it is envisioned that the snap dome 255a, 255b may be dimensioned such that the point of inversion of the snap dome 255a, 255b can be coupled with a physical and audible "snap" which can be readily felt or heard by the surgeon thus enhancing the surgeon's control over the activation of the instrument.

As best shown in FIG. 4, backer plate assembly 260 includes generally symmetrical backer plates 261a and 261b each dimensioned to securely retain and support a respective dome switch 252a and 252b thereon. More particularly, each backer plate, e.g., 261b, includes a series of mechanical interfaces or raised ledges 264a and 264b which are configured to support and secure a respective dome switch, e.g., dome switch 252b, therebetween. Recesses (not shown) or a combination of ledges and recesses may also be utilized to accomplish the same or similar purpose, e.g., securely mounting the dome switches 252a and 252b. Preferably, the dome switches 252a and 252b are assembled and secured to the backer plates 261a and 261b using a snap-fit mechanical interface but other mechanical interfaces are also envisioned to accomplish the same or similar purpose, e.g., adhesives, key-like interfaces, welding, screws, etc. The two backer plates 261a and 261b may be symmetrical which reduces production costs and facilitates assembly.

During assembly, the backer plates 261a and 261b are initially secured within housing 101. Alternatively, the backer plates 261a and 261b may be formed integrally with the housing 101 during an initial manufacturing step. FCB 250 is then secured to each backer plate 261a and 261b by orienting each dome switch 252a and 252b between the various mechanical ledges 264a and 264b extending from each outer-facing side of each backer plate 261a and 261b. Alternatively, the FCB 250 may be secured to the backer plates 261a and 261b and then the FCB 250 and backer plates 261a and 261b may then be secured to either side of the halves 101a and 101b of the housing 101. Once secured and as shown in FIG. 4, the FCB 250 wraps around the backer plates 261a and 261b such that the terminal connections 265a and 265b reside therebetween. As mentioned above, various bend points 259 may be configured within the FCB 250 to facilitate wrapping around the backer plates 261a and 261b.

Figure 5:
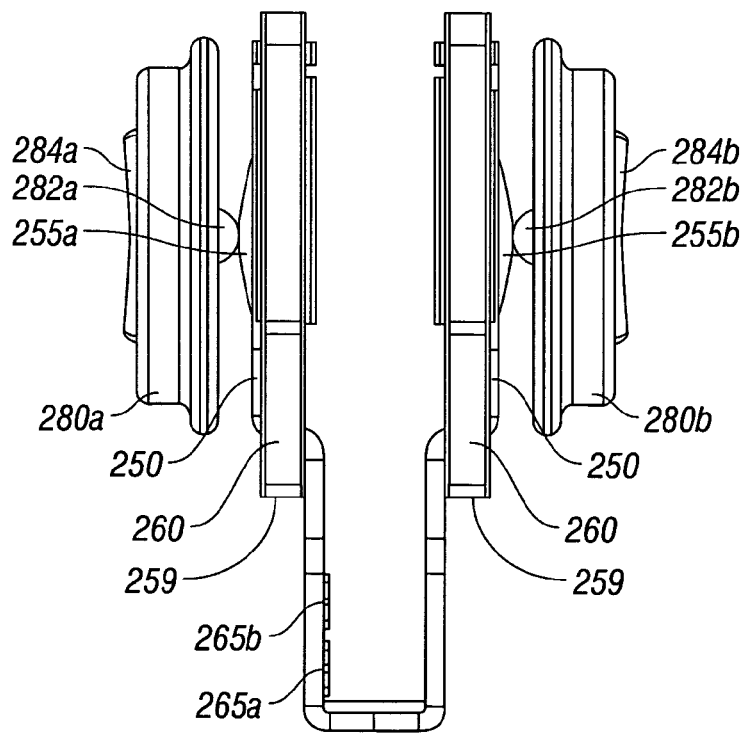
FIG. 5 is a front view of a handswitch of the handswitch and disposable electrode assembly shown assembled.

FIGS. 3C and 5 show rear views of the dome switches 252a and 252b mounted atop the backer plates 261a and 261b, respectively, in registration with two activation buttons 280a and 280b. More particularly, each activation button 280a and 280b includes a contoured ergonomically-friendly outer profile 284a and 284b which facilitates activation of the activation switch 280a and 280b by the user. A detent 282a and 282b is associated with each switch 280a and 280b which operatively connects to a respective apex 251a and 251b of each dome switch 252a and 252b. Once assembled, transverse or lateral movement of an activation button, e.g., button 280a, inverts the respective dome switch, e.g., 252a, into communication with the FCB 250 to activate the electrode assembly 100. The two dome switches 252a and 252b disposed on either side of housing 101 operatively communicate with activation buttons 280a and 280b, respectively, to independently control activation of the electrodes 110 and 120.

Figure 8A:
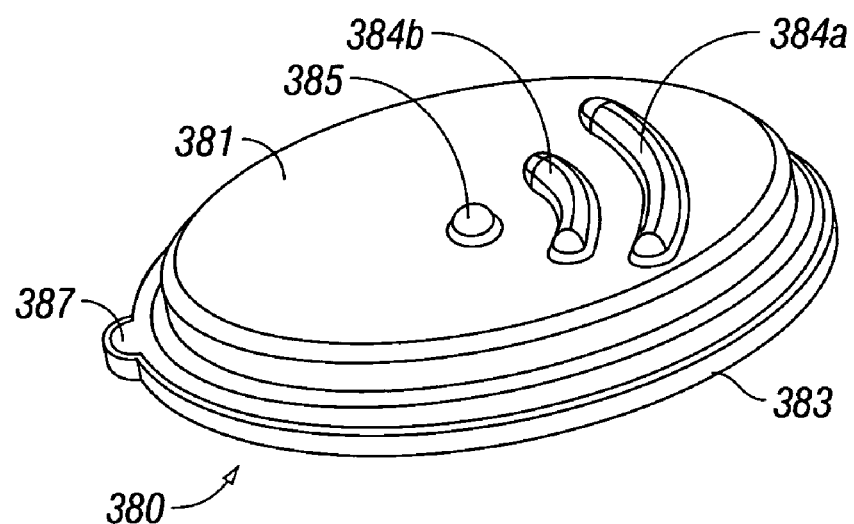
FIGS. 8A-10B are enlarged views of various designs of a handswitch activation button for use with the handswitch and disposable electrode assembly.
Figure 8B:
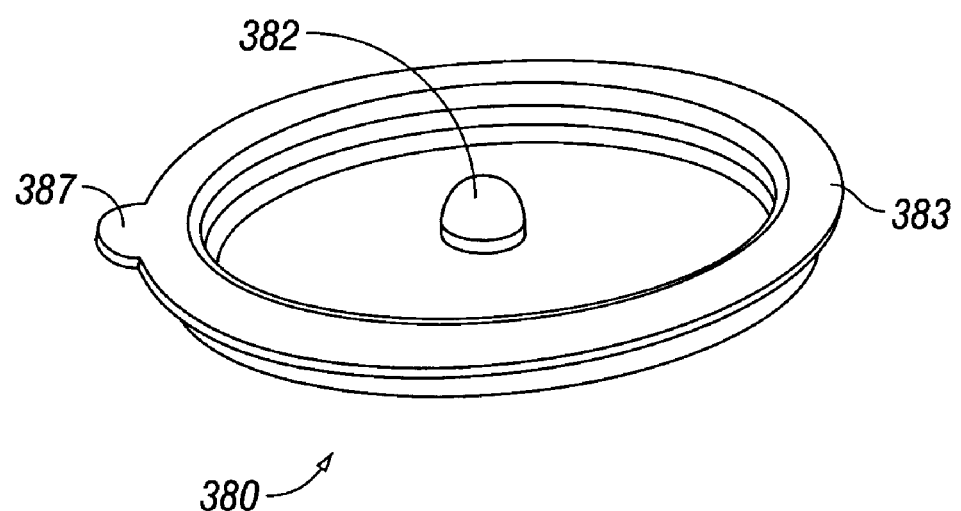

FIGS. 8A-10B show various activation button designs for use with the forceps 10 of the present disclosure. FIGS. 8A and 8B show one alternate embodiment of an activation button 380 which includes a finger-engagement surface 381 having a series of tactile features disposed thereon. More particularly, button 380 includes one or more curved raised protuberances 384a and 384b which extend from the finger-engaging surface 381 and which are configured to provide enhanced positive engagement for an operator's finger on the button 380 during use, especially under wet operating condition. A centrally disposed raised protuberance 385 is also included which is configured to align the operator's finger in vertical registration with an underlying detent 382 disposed on the underside of button 380. Detent 382, operatively engages the apex , e.g., apex 251a, of dome switch 252a to activate the forceps 10 as described above.

An outer flange or rim 383 is disposed around the outer periphery of engagement surface 381 and is configured to both limit Unnecessary movement of the button 380 within housing 101 and act as a seal to reduce fluid ingress. In other words, flange 383 may hermetically-seal button 380 to housing 101 to avoid damage to the FCB 250 during wet operating conditions. A guidance tab 387 may also be included which facilitates assembly and also acts to limit unwanted button movement relative to the housing 101. Preferably, the button 380 is symmetrical about the button's 380 major axis (not shown) to reduce manufacturing costs and ease assembly.

Figure 9A:
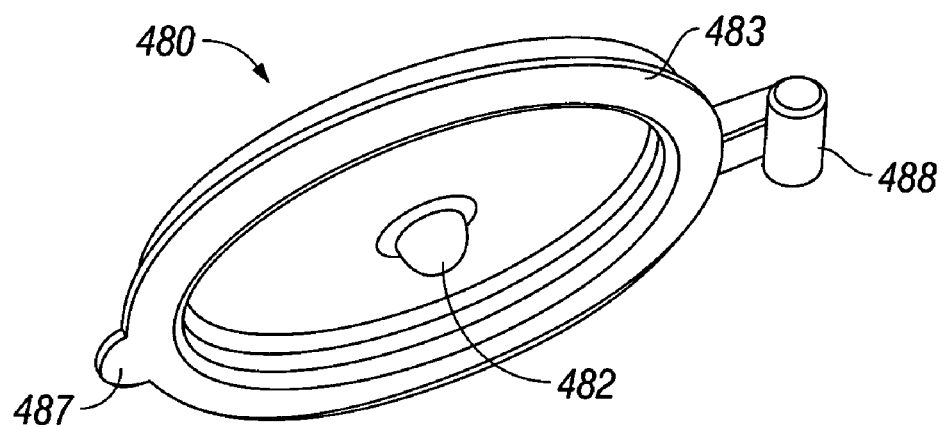
Figure 9B:
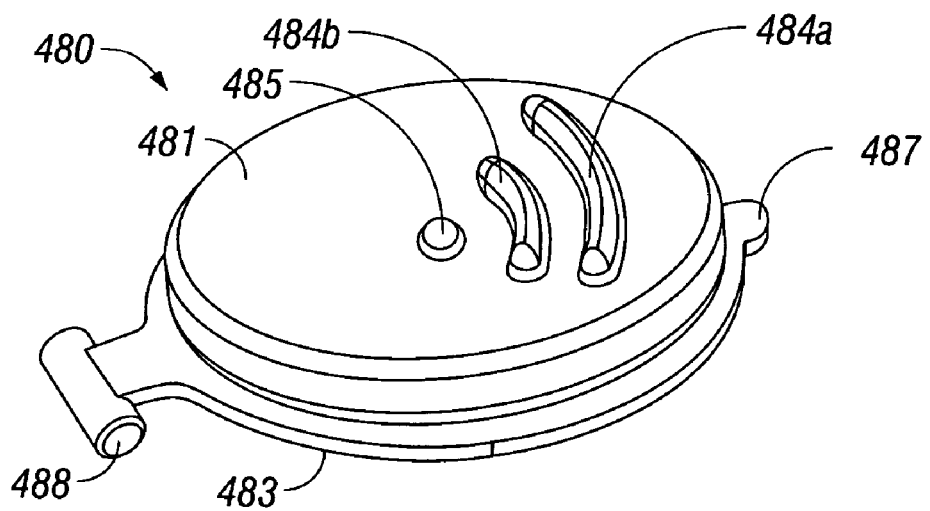

FIGS. 9A-10B show alternate embodiments of activations buttons for use with the presently disclosed forceps 10. FIGS. 9A and 9B show an activation button 480 which includes similar elements as described above with respect to FIGS. 8A and 8B (e.g., finger-engagement surface 481, outer flange 483, tactile features 484a, 484b and 485, guidance tab 487 and detent 482) with the exception of a rocker pivot 488 disposed opposite the guidance tab 487. It is envisioned that the rocker pivot 488 provides enhance tactile feel of the movement of the underlying dome switch, e.g., 255a, during activation and release due to the majority of the leverage being directed towards the proximal portion of the button 480. It is also envisioned that the positioning of the pivot 488 towards the proximal portion of the button 480 greatly facilitates the overall tactile feel of the activation button 480 and allows a surgeon to simply pull the button 480 proximally which facilitates activation. Moreover, the combination of the pivot 488 and guidance tab 487 is believed to also enhance stability of the button 480 during activation and reduce any wobble effect.

Figure 10A:
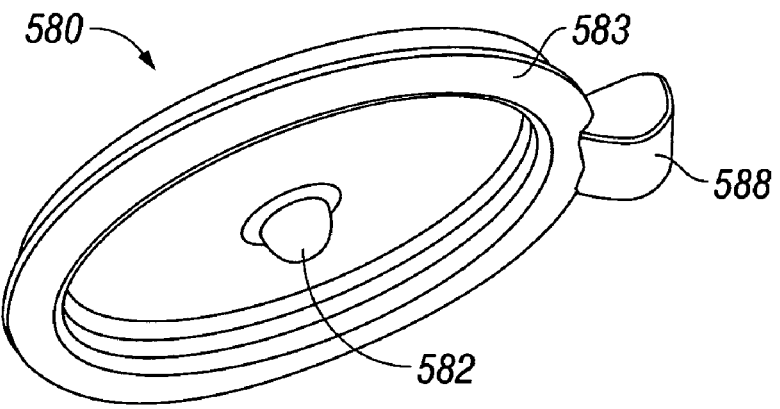
Figure 10B:
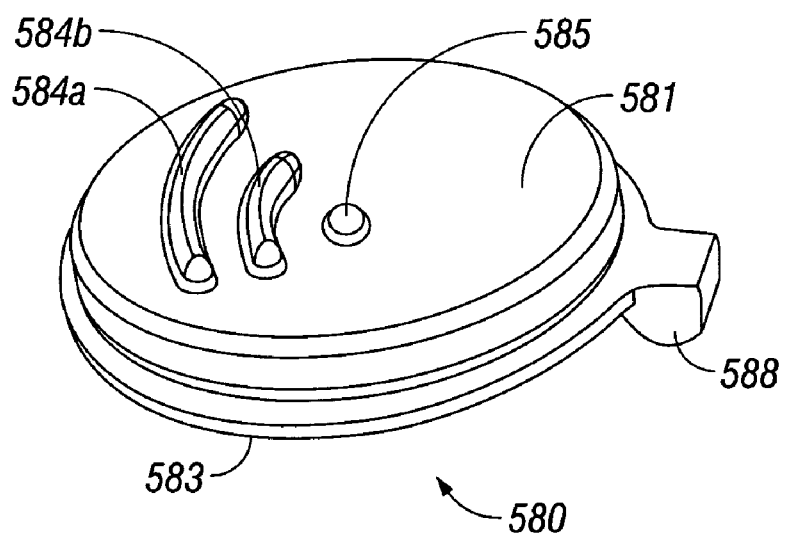

FIGS. 10A and 10B show yet another activation button 580 which, again, includes similar elements as described above with respect to FIGS. 8A and 8B (e.g., finger-engagement surface 581, outer flange 583, tactile features 584a, 584b and 585, and detent 582) and includes an alternate design of a forwardly-disposed rocker pivot 588.

Electrical leads 60 and 62 are electrically connected to the FCB 250 such that when the handswitch assembly 200 is depressed, lead 62 carries the first electrical potential from the FCB 250 to electrode 110 and a second electrical potential is carried by lead 60 directly from the generator (not shown) to electrode 120. It is envisioned that a safety switch or circuit (not shown) may be employed such that handswitch assembly 200 cannot fire unless the electrodes 110 and 120 are closed and/or unless the electrodes 110 and 120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 the entire contents of which are hereby incorporated by reference herein.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16a and 16b is required to deflect the electrodes in the same plane.

Other types of handswitch assemblies are also envisioned, for example, a regular push-button style handswitch or a toggle switch which permits the user to selectively activate the electrode assembly 100 in a variety of different orientations, i.e., multi-oriented activation, which simplifies activation. For example, FIGS. 1B-1C show a recessed handswitch assembly 200' for use with the forceps 10. More particularly, a recessed activation button 680 may be disposed within a recess 681 defined in the housing 101 and utilized with forceps 10 to facilitate activation. It is envisioned that positioning the button 680 within a recess in this fashion provides enhanced feel to the instrument and provides a flush profile. Other types of handswitches are disclosed in commonly-owned, co-pending U.S. patent application Ser. No. 10/460, 926 the entire contents of which are hereby incorporated by reference herein.

Although it is preferable to vertically align electrodes 110 and 120, in some cases it may be preferable to offset the opposing electrodes 110 and 120 relative to one another either longitudinally or transversally to suit a particular purpose.

FIG. 1A shows one envisioned proximal portion 102 while FIG. 1C shows a variation of the proximal portion 102a of the housing 101 which is configured to direct the instrument cable 300 away from the operator's palm when using the instrument in a palm-like fashion.

While various embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A removable handswitch assembly comprising:
   a housing having at least one portion adapted to removably engage at least a portion of a mechanical forceps;
   a handswitch disposed on said housing, said handswitch adapted to connect to an electrosurgical generator and including:
      a backer plate; and
      a flexible circuit board configured to wrap around the backer plate and electrically connect to the electrosurgical generator;
   a pair of electrodes removably engageable with a distal end of said mechanical forceps such that said electrodes reside in opposing relation to one another, at least one electrode being adapted to connect to the electrosurgical generator through the flexible circuit board of said handswitch; and
   at least one stop member operatively associated with at least one of said electrodes which controls the distance between said opposing electrodes.

2. A removable handswitch assembly according to claim 1 wherein said stop member is proximal to said electrodes.

3. A removable handswitch assembly according to claim 1 wherein said handswitch includes at least one activation button disposed on one side of said housing.

4. A removable handswitch assembly according to claim 1 wherein said handswitch includes two activation buttons disposed on said housing.

5. A removable handswitch assembly according to claim 4 wherein each of said activation buttons operatively cooperate with the flexible circuit board to control activation of said electrodes.

6. A removable handswitch assembly according to claim 1 wherein said handswitch includes at least one dome switch disposed within said housing which operatively connects to the flexible circuit board to control the activation of said electrodes.

7. A removable handswitch assembly according to claim 6 wherein said backer plate supports said at least one dome switch within said housing.

8. A removable handswitch assembly according to claim 7 wherein said backer plate includes at least one mechanical interface which secures said dome switch thereto.

9. A removable handswitch assembly according to claim 6 wherein said flexible circuit board includes at least one resistor which controls current though said handswitch.

10. A removable handswitch assembly according to claim 1 wherein said handswitch includes two dome switches disposed within said housing which operatively connect to the flexible circuit board to control the activation of said electrodes.

11. A removable handswitch assembly according to claim 10 wherein said housing includes two housing halves which matingly engage one another to form said housing and said flexible circuit board is dimensioned to span between said two housing halves prior to assembly.

12. A removable handswitch assembly according to claim 11 wherein said handswitch includes one backer plate operatively associated with each housing half which supports one of said two dome switches within said housing and said flexible circuit board is configured to wrap around both of said backer plates within said housing at assembly.

13. A removable handswitch assembly comprising:
    a housing having at least one portion adapted to removably engage at least a portion of a mechanical forceps; and
    a handswitch disposed on said housing adapted to connect to an electrosurgical generator, said handswitch including:
       a backer plate; and
       a flexible circuit board configured to wrap around the backer plate and having at least one portion thereof which operatively communicates with at least one activation button to control the activation of a pair of electrodes, said electrodes being removably engageable with a distal end of said mechanical forceps such that said electrodes reside in opposing relation to one another.

14. A removable handswitch assembly according to claim 13 wherein said activation button includes a rocker pivot at one end thereof which allows the activation button to pivot into operative communication with said flexible circuit board.

15. A removable handswitch assembly according to claim 13 wherein said activation button is affixed to one side of said housing.

16. A removable handswitch assembly according to claim 15 wherein said activation button includes a guidance tab at one end thereof which facilitates alignment and assembly of said activation button atop said flexible circuit board and within said housing.

17. A removable handswitch assembly according to claim 13 wherein said flexible circuit board includes two dome switches disposed on either side of said housing which operatively communicate with two corresponding activation buttons to independently control activation of said electrodes.

18. A removable handswitch assembly according to claim 17 wherein said housing includes two housing halves which matingly engage one another to form said housing and said flexible circuit board is dimensioned to span between said two housing halves prior to assembly.

19. A removable handswitch assembly according to claim 18 wherein said backer plate operatively couples to each housing half which supports one of said two dome switches within said housing.

20. A removable handswitch assembly comprising:
    a housing having at least one portion adapted to removably engage at least a portion of a mechanical forceps; and
    a pair of electrodes removably engageable with a distal end of said mechanical forceps such that said electrodes reside in opposing relation to one another, at least one electrode being adapted to connect to an electrosurgical generator through a handswitch, said handswitch including:

a backer plate; and a flexible circuit board configured to wrap around the backer plate and having at least one portion thereof which operatively communicates with an activation button to control the activation of said pair of electrodes, said activation button disposed in a recess defined in a side of said housing.

* * * * *